United States Patent [19]

Parthasarathy et al.

[11] 4,280,959

[45] Jul. 28, 1981

[54] OXIDATIVE DEHYDROGENATION OF ALKENES OR ALKADIENES TO FURAN COMPOUNDS

[75] Inventors: R. Parthasarathy; Eugene V. Hort, Wayne, both of N.J.

[73] Assignee: GAF Corporation, New York, N.Y.

[21] Appl. No.: 189,451

[22] Filed: Sep. 22, 1980

[51] Int. Cl.$^3$ .......................................... C07D 307/36
[52] U.S. Cl. ............................. 260/346.11; 252/437
[58] Field of Search .................................... 260/346.11

[56] References Cited

U.S. PATENT DOCUMENTS

| | | | |
|---|---|---|---|
| 3,271,459 | 9/1966 | Brill et al. | 260/604 |
| 3,716,545 | 2/1973 | Ripley | 260/346.11 |

*Primary Examiner*—Henry R. Jiles
*Assistant Examiner*—Bernard Dentz
*Attorney, Agent, or Firm*—James Magee, Jr.; Walter Katz

[57] ABSTRACT

Alkenes and/or alkadienes are contacted with molecular oxygen and an oxidative dehydrogenation catalyst consisting essentially of silver, phosphorus and oxygen, with the silver-to-phosphorus atom ratio being in the range of about 0.25:1 to about 10:1 to produce furan compounds.

4 Claims, No Drawings

OXIDATIVE DEHYDROGENATION OF ALKENES OR ALKADIENES TO FURAN COMPOUNDS

BACKGROUND OF THE INVENTION

1. Field of the Invention

This invention relates to oxidative dehydrogenation catalysts and the use thereof for the conversion of alkenes and/or alkadienes to furan compounds.

2. Description of the Prior Art

Furan compounds can react readily with oxygen under oxidation conditions to produce ring cleavage and the formation of polymers. Accordingly, the production of furan compounds by the oxidative dehydrogenation of hydrocarbons has generally been avoided. Recently it has been discovered that furan compounds can be produced effectively by the oxidative dehydrogenation of hydrocarbons in the presence of certain specific catalysts. Accordingly, the search for additional catalysts suitable for this reaction continues.

The state of the prior art is exemplified particularly by U.S. Pat. Nos. 3,906,009, 3,894,055, 3,928,389, 3,912,763, 4,039,476 and 4,026,820. The catalyst systems disclosed in these patents, however, are not especially selective in forming only furan under the process conditions. Instead, a considerable portion of the alkene or alkadiene starting material is converted to undesired aldehydes, ketones, or oxidized to carbon oxides and water.

Therefore, it is the object of the present invention to provide a new and improved oxidative dehydrogenation catalyst for the conversion of alkenes or alkadienes to furan compounds which is highly selective in oxidizing butadiene to furan in the vapor phase.

SUMMARY OF THE INVENTION

In accordance with the present invention, there is provided an improved catalyst for the production of furan type compounds from alkenes and alkadienes having from 4 to 10 carbon atoms, which catalyst consists essentially of silver, phosphorus and oxygen, wherein the silver-to-phosphorus atom ratio is suitably in the range of about 0.25:1 to about 10:1, preferably in the range of about 0.5:1 to about 8:1, and, in the best mode, in the range of about 1:1 to about 5:1.

DETAILED DESCRIPTION OF THE INVENTION

If desired, the novel, improved catalysts of the invention can be supported on conventional solid catalytic support materials, for example, zinc oxide, silica, alumina, boria, magnesia, titania, zirconia, and mixtures thereof. Where a catalyst support is employed, the support will generally constitute from about 10 to about 98, preferably from about 75 to about 95, weight percent of the total catalyst composition. Supports having a surface area in the range of about 2 to about 50 m$^2$/g, and preferably in the range of about 5 to about 20 m$^2$/g, are desirable.

The catalysts of the present invention can be prepared by a wide variety of techniques, for example, coprecipitation, impregnation, or aqueous or non-aqueous solution or suspension mixing. In the preferred embodiment of this invention, the catalyst is prepared by coprecipitation of water soluble silver and phosphorus compounds, such as silver nitrate and phosphoric acid, followed by drying and calcination. Any compound of silver or phosphorus can be used in preparing the catalyst as long as all of the elements other than silver, phosphorus and oxygen are removed from the final catalyst by washing or by volatalization. However, trace amounts of other elements, such as alkali or alkaline earth and transitional metals, are not detrimental. Generally, the preferred compounds of silver and phosphorus are those easily converted to the oxides on calcination. Examples of these are the acids, nitrates, acetates and other carboxylates, hydroxides and the like.

Unsupported catalysts may be used as well. One technique for forming an unsupported catalyst comprises mixing one or more silver compounds, and one or more phosphorus compounds.

The compounds can be admixed in the form of dry compounds and then calcined. They can be mixed in the presence of a diluent to form a paste and/or one of the components can be employed in liquid form, such as silver nitrate solution, to form the paste. If desired, the paste can be dried before calcining. A particle forming step such as pelletizing or screening can precede the drying step or the calcining step.

In the preferred technique for producing the catalyst of present invention, silver phosphate is precipitated by admixing aqueous solutions of silver nitrate and phosphoric acid. Then a suitable diluent; such as fine particle α-Al$_2$O$_3$ or titanium dioxide is added and the paste is dried and calcined. A particle forming step, such as pelletizing or pilling, may precede the drying or calcination, if desired.

The calcining step itself comprises heating the catalyst composition to a temperature in the range of about 250° C. to about 650° C. for about 0.5 to about 24 hours preferably at a temperature range of 400° C.–600° C. for about 2–16 hrs., in the presence of an oxygen-containing gas, such as air.

Suitable feeds for conversion to furan compounds include the unsaturated acyclic hydrocarbons, particularly the acyclic alkenes and acyclic alkadienes having from 4 to 10 carbon atoms. Examples include n-butene-1, butene-2, n-pentene-1, isopentene, hexene-1, heptene-2, octene-1, decene-1, 2-methylbutene-1, hexene-3, 2-ethylbutene-1, 2-methylpentene-3, 3-ethylhexene-2, butadiene-1,3, pentadiene-1,3, isoprene, hexadiene-1,3, decadiene-1,3, pentadiene-1,3, and the like, and mixtures thereof. The acyclic alkadienes having from 4 to 5 carbon atoms are presently preferred.

The furan compounds produced by the process of the present invention have the formula:

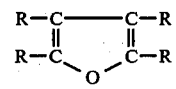

wherein each R is individually selected from the group consisting of hydrogen and alkyl radicals having from 1 to 6 carbon atoms, the total carbon atoms in the R radicals being in the range of 0 to 6. Representative products include furan, 2-methylfuran, 3-methylfuran, 2,5-diethylfuran, 2-n-hexylfuran, 2-isopropyl-3-methylfuran, 3,4-di(n-propyl)furan, 3-methyl-4-n-butylfuran and the like.

In the process, a hydrocarbon feed comprising of one or more acyclic alkenes and/or one or more acyclic alkadienes is contacted under suitable reaction conditions with oxygen-containing gas for conversion to furan compounds in the presence of the above-defined catalyst. The temperature used is in the range of 200° C. to 600° C., preferably in the range of 250°–450° C. Any suitable pressure can be employed, but, in general, the pressure ranges from 0.05 to about 200 psig. and preferably in the range of about 0.1 to 25 psig. The total gas rate may be in the general range of about 50 to 5000 standard volumes per hour per volume of catalyst bed (GHSV) and preferably in range of about 100 to 4000 (GHSV). The mol ratio of oxygen to alkenes and alkadienes will generally be in the range of about 0.1:1 to about 10:1, and preferably in the range of 0.5:1 to about 6:1. Steam can be employed in the reaction zone as an inert diluent and a heat carrier, suitably in the mol ratio of steam to alkenes and alkadienes of about 0.5:1 to 50:1, and preferably from about 5:1 to about 25:1.

The alkenes, if present, are converted mostly to corresponding alkadienes, which, in turn, are converted in significant quantities to furan compounds. However, the reaction effluent can also contain unreacted feed material, lower alkenes, such as ethylene and propylene; water, oxides of carbon, aldehydes, such as crotonaldehyde, acetaldehyde and acrolein; ketones, such as acetone, methyl ethyl ketone and methyl vinyl ketone; and other oxygenated products. Unconverted alkenes and/or alkadienes can be recovered and recycled to the reactor as can other partial oxygenated products, such as crotonaldehyde, which are convertible to furan compounds under the reaction conditions.

The following examples are presented in further illustration of the invention and should not be construed in undue limitation thereof.

EXAMPLE 1

Preparation of Catalyst 11.5 g phosphoric acid (85%) in 10 ml water was added dropwise to 17 g (0.1 mol) of silver nitrate in 15 ml water to form silver phosphate precipitate. Then 6.2 g of fine particle titanium dioxide was uniformly blended into the precipitate and the whole mass was evaporated to dryness over a steam bath, dried further at 120° overnight, and calcined for 3 hours at 400° C. The resultant mass was ground into catalyst particles having a diameter of about 2–4 mm. The Ag/P atom ratio of this catalyst was 1:1.

EXAMPLE 2

Process Reaction

The reaction vessel was a stainless steel tube 12 inches in length long, a 1 inch i.d. and having a ⅛″ central thermal well was packed with about 10 cc (24.1 g) of the catalyst of Example 1. Butadiene was used as the hydrocarbon feed material, and nitrogen up to 50% was used as a diluent in all the tests. The results are reported in the tables below, in which the terms used are defined as follows:

| | |
|---|---|
| Conversion: | Percentage of starting material, e.g. butadiene, consumed in the reaction. |
| Selectivity: | Percentage of a particular product, e.g. furan, produced in the process, based on the total starting material consumed. |
| Aldehydes: | Acetaldehyde, acrolein and crotonaldehyde. |
| Other: | Acetone and $C_4$—ketones. |
| Carbon oxides: | $CO$ and $CO_2$. |
| $C_4=$: | Butadiene. |

TABLE 1

| Reaction Time (Hrs) | Press. (Atm) | $O_2/C_4=$ | Contact Time (Secs) | Temp. (°C.) | $C_4=$ Conv (%) | Furan (%) | Aldehydes (%) | Carbon Oxides (%) |
|---|---|---|---|---|---|---|---|---|
| 1 | 1 | 2–4 | 4 | 258 | 2 | 73 | 10 | 17 |
| 4 | 1 | 2–4 | 4 | 258 | 0.8 | 57 | 13 | 31 |
| 9 | 1 | 2–4 | 4 | 276 | 2 | 49 | 15 | 32 |
| 5 | 1 | 2–4 | 3 | 400 | 8 | 36 | 2 | 62 |

The results show an effective and selective conversion to furan.

EXAMPLE 3

In this example, a silver phosphate catalyst containing a silver-to-phosphorus ratio of 3 was used, which was higher than the stoichiometric ratio. The catalyst was prepared as follows.

5 g of silver phosphate and 5 ml. water were mixed together to form a slurry, 2.1 g $\alpha$-$Al_2O_3$ was uniformly blended in, and the mass was evaporated to dryness over a steam bath. Thereafter it was dried for 1 hr. at 120° C. in a vacuum oven, and the resulting mass was calcined for 3 hrs. at 400° C. in a muffle furnace and ground into particles of 2 to 4 mm.

The results are shown in Table 2 below.

TABLE 2

| Reaction Time (Hrs) | Press. (Atm) | $O_2/C_4=$ | Contact Time (Secs) | Temp. (°C.) | $C_4=$ Conv (%) | Furan (%) | Aldehydes (%) | Carbon Oxides (%) |
|---|---|---|---|---|---|---|---|---|
| 12 | 1 | 2–4 | 5 | 344 | 8 | 45 | 12 | 43 |

The results in Table 2 demonstrate that a catalyst with a Ag/P ratio of 3:1 also is effective in producing substantial amounts of furan from a relatively modest conversion of butadiene.

What is claimed is:

1. A process which comprises reacting at least one unsaturated acyclic feed hydrocarbon selected from the group consisting of alkenes and alkadienes having from 4 to 10 carbon atoms, with oxygen in contact with a catalyst composition consisting essentially of silver, phosphorus and oxygen, with the silver-to-phosphorus atom ratio being in the range of 0.25:1 to about 10:1, under suitable vapor-phase reaction conditions for the conversion of said at least one unsaturated acyclic feed hydrocarbon to at least one furan compound having the formula

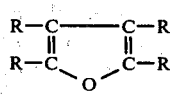

wherein each R is individually selected from the group consisting of hydrogen and alkyl radicals having from 1 to 6 carbon atoms, the total carbon atoms in the R radicals being in the range of 0 to 6; and recovering at least a portion of the furan compounds thus produced, wherein said reaction conditions comprise a temperature in the range of about 200° C. to about 600° C., an unsaturated acyclic hydrocarbon feed rate in the range of about 10 to about 1000 GHSV, and a mol ratio of oxygen to unsaturated acyclic feed hydrocarbon in the range of about 0.1:1 to about 3:1.

2. A process in accordance with claim 1 wherein said feed hydrocarbon comprises at least one acyclic alkadiene having from 4 to 5 carbon atoms.

3. A process in accordance with claim 2 wherein said silver-to-phosphorous atom ratio is in the range of about 0.5:1 to about 8:1.

4. A process in accordance with claim 3 wherein said feed hydrocarbon comprises butadiene and said composition further consists essentially of a solid support.

* * * * *